United States Patent [19]

Obermajer

[11] 4,035,622

[45] July 12, 1977

[54] APPARATUS FOR MEASURING THE CARDIAC CAPACITY

[76] Inventor: Wladimir Obermajer, 1 villa Leandre, 75018 Paris, France

[21] Appl. No.: 632,908

[22] Filed: Nov. 18, 1975

[30] Foreign Application Priority Data

Nov. 20, 1974  France .......................... 74.38101

[51] Int. Cl.² .................. G06F 15/42; A61B 5/02
[52] U.S. Cl. ...................... 235/151.3; 128/2.05 F; 128/2.05 V
[58] Field of Search ........... 235/151.3; 128/2.05 R, 128/2.05 F, 2.05 V

[56] References Cited

U.S. PATENT DOCUMENTS

| | | | |
|---|---|---|---|
| 3,304,413 | 2/1967 | Lehmann et al. | 235/151.3 X |
| 3,527,542 | 9/1970 | Penhasi et al. | 128/2.05 R X |
| 3,618,591 | 11/1971 | Bradley et al. | 128/2.05 F |
| 3,651,318 | 3/1972 | Czekajewski | 128/2.05 F X |
| 3,677,648 | 7/1972 | Dorsch | 128/2.05 V UX |

*Primary Examiner*—Jerry Smith

[57] ABSTRACT

The invention relates to a process for measuring the cardiac capacity or cardiac stasis at each heart beat V by dilution of the indicator (stain or frigories) injected above the heart, as well as an apparatus for performing this process.

According to the invention, a quantity $Q_i$ of indicator is injected at a constant flow rate $D_i$ for a time $t_i$ corresponding to at least two heart beats, wherein the concentration of indicator in the blood (or the temperature variation in the blood) is measured at the end of indicator injection $\Delta_m$ and $\Delta(t)$ being the indicator concentration (or temperature variation) as a function of the time t assuming $t = 0$ at the start of the injection, $t_m$ being the time at the end of the injection, the integrals $$S = \int_0^\infty \Delta(t)dt \text{ and } S' = \int_{t_m}^\infty \Delta(t)dt,$$

are measured and then the cardiac capacity (V) is deduced from the thus measured values.

3 Claims, 1 Drawing Figure

U.S. Patent     July 12, 1977     4,035,622
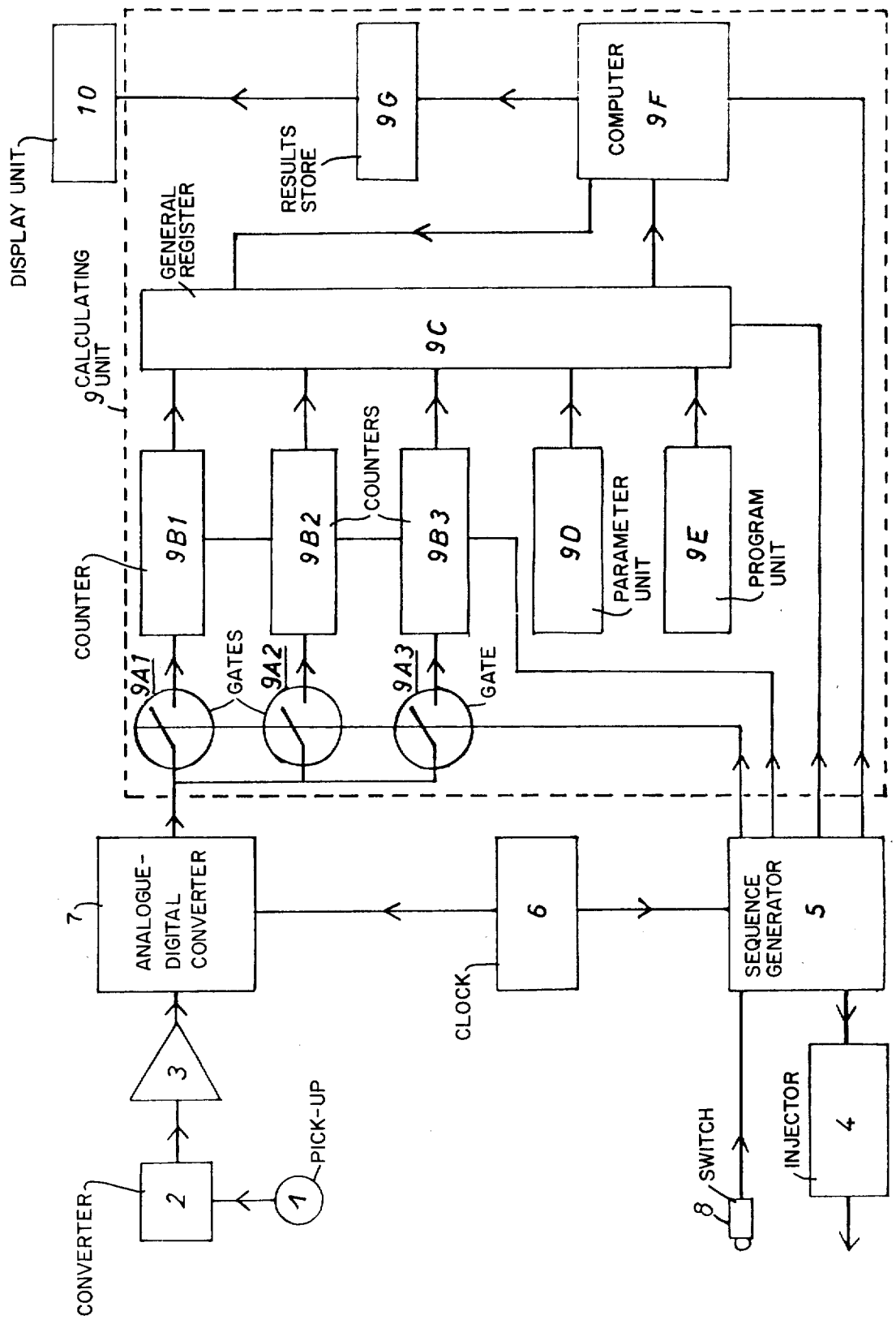

APPARATUS FOR MEASURING THE CARDIAC CAPACITY

BACKGROUND OF THE INVENTION

The present invention relates to a process and apparatus for measuring the cardiac capacity, and more particularly the cardiac stasis, i.e. the quantity of blood in the heart between one heart beat and the next.

Dilution methods and more particularly those using stains or the injection of a cold liquid (thermodilution) are used for measuring the cardiac output. This output can be given by the following formula:

$$\overline{D} = \frac{Q_i}{\int_0^\infty \Delta(t)dt} \quad (1)$$

in which:
$\overline{D}$ is the average circulation rate,
$Q_i$ is the total quantity of the indicator or marker injected above the hear (stain or frigories),
$\Delta(t)$ is the concentration of the indicator or the temperature variation at the outlet from the heart as a function of the time $t$, basing these times on the moment of starting the injection of the indicator or a previous time.

In connection with measuring the cardiac capacity (ventricular capacity, auricular capacity or total capacity) attempts have been made using more particularly two processes:

The first consists of comparing the curve $\Delta(t)$ after the end of injection with a decreasing exponential and deducing therefrom the ventricular capacity. However, either the indicator is injected into the ventricle, in which case the lack of homogeneity of the mixture leads to considerable errors, or the injection takes place into the auricle or above it, in which case it can be shown that the decreasing curve $\Delta(t)$ is the sum of two distinct exponentials and that the comparison with one exponential leads to considerable errors.

The second known process is based on the following argument:

Assuming that at time $t_o$ a certain quantity $Q_i$ of the indicator is instantaneously injected, the curve $\Delta(t)$ can then be considered as a histogram as a function of time and the length of stay of the indicating elements (stain molecules or frigories) in the heart, the mean value $\overline{t}$ of this length of stay can be calculated by the ratio:

$$\overline{t} = \frac{\int_0^\infty t\Delta(t)dt}{\int_0^\infty \Delta(t)dt} \quad (2)$$

by accepting the hypothesis that the molecules of blood have the same length of stay as those of the indicator, the volume V occupied by the blood can be calculated by using the following formula:

$$V = \overline{D} \times \overline{t} = Q_i \frac{\int_0^\infty t\Delta\, dt}{(\int_0^\infty \Delta\, dt)^2} \quad (3)$$

Thus this calculation assumes an instantaneous injection. However, in practice for mechanical reasons it is impossible to reduce its duration to below a considerable fraction of a second, which leads to a considerable error, $\overline{t}$ normally being of the order of one to three seconds, and moreover due to the mechanical reaction caused by the stream of indicator causes a movement of the catheter so that successive measurements cannot be compared.

It would still be possible to use this process by carrying out a non-instantaneous injection. For this it would be necessary on the basis of a histogram as a function of time and the quantities of indicator injected to calculate an average injection time lag $\overline{t}_o$ relative to the start of the injection and to substitute in the formula (3): $\overline{t} - \overline{t}_o$ to $\overline{t}$. The difficulties of carrying out such a process are obvious in that it requires besides the measuring integral of the output the measurement of one or two supplementary integrals making separate and complex calculating devices necessary.

Moreover, in view of rapidity of elimination of the indicator it is obvious that this method is very sensitive to the time of injection relative to the phase of the cardiac cycle, whereby the error for this reason alone can reach 25 percent.

BRIEF SUMMARY OF THE INVENTION

The process forming the object of the present invention has totally different bases. It is substantially based on the fact that if there is a continuous injection of the indicator and at a constant flow rate, after a short time the indicator concentrations in the different parts of the heart reach a stationary state. The calculation shows that for a normal heart three or four heart beats suffice for reaching this state with a very good degree of approximation.

$Q_i$ being the total quantity of indicator which it is proposed to inject, we will call $q(t)$ the quantity of indicator present at time $t$ above the measuring point of $\Delta(t)$ in the heart and in the injection device: $q(O) = Q_i$, $q(\infty) = 0$ It is therefore possible to write:

$$\overline{D} = \frac{q(t_m)}{\int_{t_m}^\infty \Delta(t)dt} \quad (4)$$

which is similar to (1) and wherein $t_m$ is a priori a random time.

After carrying out an injection with a uniform flow rate for a time sufficient to come close to the stationary state, the injection is suddenly stopped at time $t_m$ so that the quantity of indicator present in the heart is obviously $q(t_m)$. By combining (1) and (4), we find:

$$q(t_m) = Q_i \frac{\int_{t_m}^\infty \Delta(t)dt}{\int_0^\infty \Delta(t)dt} \quad (5)$$

The two integrals only differ by the initial value of variable $t$.

Moreover, when the stationary state is reached, the concentration $\Delta_m$ of the indicator in the heart is substantially uniform and constant, being given by the formula:

$$\Delta_m = \frac{D_i}{D} \quad (6)$$

$D_i$ being the flow of indicator (stain or frigorie).
Moreover, obviously:

$$\Delta_m = \frac{q(t_m)}{V} \quad (7)$$

V being the volume of blood present in the heart at time $t_m$.

The combination of (5) and (7) gives us the ratio:

$$V = \frac{Q_i}{\Delta_m} \cdot \frac{\int_{t_m}^{\infty} \Delta(t)dt}{\int_0^{\infty} \Delta(t)dt} \quad (8)$$

This ratio can also be written:

$$V = \frac{\overline{D}}{\Delta_m} \int_{t_m}^{\infty} \Delta(t)dt \quad (9)$$

By combining (6) and (9) and calling $t_i$ the length of injection, we find:

$$V = \frac{\overline{D}^2}{Q_i} t_i \int_{t_m}^{\infty} \Delta(t)dt \quad (10)$$

which can also be written:

$$V = Q_i t_i \frac{\int_{t_m}^{\infty} \Delta(t)dt}{(\int_0^{\infty} \Delta(t)dt)^2} \quad (11)$$

It can be shown that the ratios (3) and (11) are equivalent if, and only if, the start of injection occurs at the start of a systole. If not, the volume calculated on the basis of (3) is erroneous, but that given by (11) remains correct. This represents an important advantage of the present invention.

The invention therefore has for its object a process for measuring the cardiac capacity or cariacd stasis at each beat V by dilution of the indicator (stain or frigories) injected above the heart, wherein a quantity $Q_i$ of indicator is injected at a constant flow rate $D_i$ for a time $t_i$ corresponding to at least two heart beats, wherein the concentration of indicator in the blood (or the temperature variation in the blood) is measured at the end of indicator injection $\Delta_m$ and $\Delta(t)$ being the indicator concentration (or temperature variation) as a function of the time $t$ assuming $t = 0$ at the start of the injection, $t_m$ being the time at the end of the injection, the integrals $$S = \int_0^{\infty} \Delta(t)dt \text{ and } S' = \int_{t_m}^{\infty} \Delta(t)dt,$$

are measured and then the cardiac capacity (V) is deduced from the thus measured values.

On comparing the calculation of V by means of (9) with that obtained by (10) in the case where the stationary state is incompletely obtained, it can be seen that for a normal heart the error is between three and four times smaller when using (9) rather than (10). However, (9) as opposed to (10) requires the measurement of $\Delta_m$. However, this is not an inconvenience if for the measurement of $\int \Delta dt$, a numerical integration process by periodic sampling of the value $\Delta(t)$ is used, when the final sample preceding the interruption of injection obviously gives the value of $\Delta_m$. Use of (9) combined with a numerical integration for the measurement of $$\int_0^{\infty} \Delta dt \text{ and } \int_{t_m}^{\infty} \Delta dt$$

forms a preferred embodiment of the present invention.

A first advantage of the process of the present invention is that only a single numerical indication form is used permitting a very great simplification of the integrations necessary for measuring the cardiac capacity.

A second advantage of this process is that it provides for the cardiac capacity measurement a result which is correct and independent of the phase relative to the cardiac cycle of the start of indicator injection.

A particular advantage of the preferred embodiment of the invention is that for a given injection period it permits a much more precise result for the measurement of the cardiac capacity, or for a predetermined precision permits a shorter injection time.

BRIEF DESCRIPTION OF THE DRAWING

The following description with reference to the drawing given as a non-limitative example relates to a device permitting the performance of the process of the present invention and more particularly according to a preferred embodiment. This device permits the simultaneous display of the cardiac output D and the cardiac capacity V. The attached drawing shows in block form the various functions whose combination constitutes the device.

DETAILED DESCRIPTION OF THE PREFERRED EMBODIMENTS

The device comprises a pick-up 1 which is fitted by catheterization upstream and as close as possible to a right or left ventricle, depending on a half-heart whose capacity and output is to be measured. This pick-up is associated with a converter 2 which transforms the quantity supplied by the pick-up, variable as a function of the indicator concentration into an electrical signal which is applied to the input of an amplifier 3. The converter 2 can optionally have a zero setting, as is the case for thermodilution where the pick-up is a thermistor. The converter is then a measuring bridge with a balancing device.

The indicator is injected by an injector 4. According to the present invention the injector 4 is an electromechanical device ensuring a constant fixed flow, e.g. 2.5 cc per second during the injection. According to a preferred embodiment, only the injection period can vary from one measurement to the next.

A sequence generator 5 controlled by a clock 6 controls the different operations, and more specifically the start and finish of injection (i.e. the injected volume) together with the numerical calculations ensured by a calculating unit 9.

Clock 6, which is preferably a quartz, crystal clock supplies a time base to sequence generator 5, but also controls an analogue-digital converter 7 which converts to the analogue signal supplied by amplifier 3 into a digital signal.

A manual release 8 which can comprise a push-button switch is connected to sequence generator 5 whose operation it initiates.

The analogue-digital converter 7 functions permanently and, at equal and sufficiently close intervals of time controlled by clock 6, it converts the voltage supplied by amplifier 3 into a pulse train whose number is proportional to the value of the said voltage. The output of converter 7 is connected to three gates 9A1, 9A2 and 9A3 included in the calculating unit 9 and controlled separately by the sequence generator 5. Each of these gates is connected to a counter 9B1, 9B2 and 9B3 whereby the said counters summate the pulses received during the opening of each gate during the same measuring operation.

Counters 9B1, 9B2 and 9B3 have a simultaneous zeroing device controlled by sequence generator 5. They are also connected to a general register 9C which collects, when controlled by sequence generator 5, the numerical values of the content of counters 9B1, 9B2 and 9B3. In the same way it collects data received by a parameter unit 9D and a programme unit 9E.

The parameter unit 9D contains in permanent or adjustable manner numerical parameters which combined with the numbers supplied by counters 9B1, 9B2 and 9B3 make available all the numerical data necessary for the calculation of the cardiac output and cardiac capacity in the desired units and as a function of the experimental conditions inherent in each measuring operation.

The programme unit 9E contains in permanent manner the instructions for the above-mentioned calculation.

The general register 9C is organized in such a way that at the command of sequence generator 5 it supplies in the correct time sequence the numeral data and instruction to a computer 9F which processes the results excepted from the apparatus. According to a preferred variant of the invention, during the calculation the empty parts of the general register 9C serve as an auxiliary store for computer 9F.

The results of the calculations supplied by computer 9F are stored in a results store 9G which in turn controls in a permanent manner, or on request, a digital display unit 10.

The device described hereinbefore operates as follows. For ease of writing we will take:

$$S = \int_o^\infty \Delta(t)dt \text{ and } S' = \int_{t_m}^\infty \Delta(t)dt$$

The cardiac output D is calculated on the basis of (1) which is written:

$$D = \frac{Q_i}{S} \qquad (12)$$

The cardiac capacity V is calculated on the basis of (9) which is written:

$$V = \frac{D}{\Delta_m} S' \qquad (13)$$

The quantity $Q_i$ which represents the indicated quantity injected is, according to the preferred procedure of the invention, proportional to the indicator injection period $t_i$. Moreover, and in particular regarding thermodilution, it can be shown that parasitic phenomena such as thermal diffusion, the special characteristics of cardiac hydrodynamics or the thermal inertia of the pick-up are equivalent, to the first order, to a multiplicative factor applied to $Q_i$ in such a way that in (12) $Q_i$ can be substituted by a factor K experimentally determined by a physical simulator and which takes overall account:

of the injected indicator concentration,
of the injection period,
and, the first order, of all parasitic phenomena linked with the measurement.

In the special case of thermodilution, it is convenient to write K in the form $k(T_s - T_i)$, $T_s$ being the blood temperature prior to injection and $T_i$ the injected liquid temperature measured outside the patient's body. In this case, k more particularly takes account:

of the injected liquid quantity,
of the heating of the liquid before it reaches the heart,
of the heat capacity per unit volume of this liquid compared with that of the blood. The ratio (12) is then written:

$$D = \frac{k(T_s - T_i)}{S} \qquad (14)$$

The operation of the device forming the object of the present invention will be described as a function of ratios (14) and (13) and in the case of the thermodilution.

Firstly, and before carrying out any real measurement, the temperature $T_s$ of the patient is taken and the factor $(T_s - T_i)$ is introduced into the parameter unit 9D according to per se known processes. The quantity k, which can for example be given by tables as a function of the type of catheter, the nature of the injected liquid and the injection flow rate is then introduced into the same unit.

When the catheter is introduced, the converter is set to zero and by means of release 8 the measuring sequence in commenced.

The sequence generator 5 actuates the automatic injector 4 at the same time as it opens gate 9A1, gates 9A2 and 9A3 being closed and counters 9B1, 9B2 and 9B3 being set to zero.

At the end of an injection period $t_i$ which can be optionally regulatable (in which case factor k must take account of this), gate 9A2 is opened for a single sampling operation, whereby counter 9B2 then contains a number proportional to $\Delta_m$. As gate 9A2 is closed, gate 9A3 is opened without delay at the same time as a sequence generator 5 interrupts the operation of automatic injector 4, followed by a sufficiently long wait for $\Delta(t)$ to become practically zero. Gates 9A1 and 9A3 are then closed. At this time, counter 9B1 contains a number proportional to S and counter 9B3 a number proportional to S'.

Sequence generator 5 then starts the loading of general register 9C, and then starts the calculating operations by means of computer 9F. General register 9C is organized in such a way that computer 9F can perform the necessary calculations in three stages.

The first stage leads to the calculation of the value of D expressed, for example, in litres per minute, for which it ensures the following operations in accordance with ratio (14):

$$k \times (T_e - T_i) \div S = D$$

the factor $k$ being determined, as indicated hereinbefore, in such a way that it takes account of the measuring characteristics, but also includes a fixed factor which, taking account of the $n$ numerical values supplied by the counters, give $D$ a numerical value expressed in the desired unit, e.g. liters per minute. According to the preferred development of the invention, the calculation of $D$ is carried out with a fixed point taking for $D$ two decimal digits, the second being accurate to one unit.

The thus calculated value of $D$ is reintroduced in a good position into general register 9C, and the second calculation stage is then performed which ensures the following operations in accordance with ratio (13):

$$D \times S' \div \Delta_m = v$$

Thus, a number $v$ is obtained which is porportional to $V$ and which must be multiplied by a factor $k'$ to obtain $V$ in a convenient unit, e. g. millilitres. According to a preferred embodiment of the invention, $v$ is calculated as a fixed point $k'$ has a limited number of significant digits, in such a way that the product $k'v = V$ only contains, for example, one decimal digit accurate to one unit.

If moreover, computer 9F is able to supply, for example, eight significant digits, as D expressed in liters per minute with two decimals has a maximum of four significant digits and V expressed in millilitres with one decimal only has a maximum of four digits, it can be seen that the operation:

$$100,00 \; k'v + D \; \text{or} \; 100,000 \; V + D$$

gives us eight digits at the output of computer 9F, whereof the first four are relative to $V$ and the four last to $D$, in such a way that after storage by 9G and display on the display unit 10, $V$ and $D$ can be read side by side, whereby the decimal points not produced by the computer are marked in a fixed position on the display unit 10.

The improvement described hereinbefore, which leads to a considerable simplification of the calculating unit 9, can form the object of numerous variants as a function more particularly of all the numerical values used. In certain cases, for example, computer 9F can have at its output 10 significant digits, whereby only eight are shown on the display unit.

The invention is not limited to the embodiments described and represented hereinbefore, numerous variants being possible thereto without passing beyond the scope of the invention.

What is claimed is:

1. An apparatus for measuring the caridac blood capacity or cardiac stasis V of a heart at each beat comprising:
    an injector, adapted to be fitted by catheterization, for injecting an indicator above the heart, forming an indicator concentration in the blood;
    a pickup, adapted to be fitted by catheterization, for providing an electrical signal $\Delta t$ variable with respect to time and indicative of the indicator concentration in the blood;
    means for measuring the quantity $\Delta_m$ corresponding to the indicator concentration in the blood at a time $t_m$ which represents the end of a sequence;
    a sequence generator for controlling said injector;
    a clock for controlling said sequence generator;
    an analogue-digital converter which is responsive to said clock and said pickup; and
    a calculating unit, responsive to said sequence generator and said analogue-digital converter, for calculating the integrals $$S = \int_o^\infty \Delta(t)dt \; \text{and} \; S' = \int_{t_m}^\infty \Delta(t)dt$$

and the ratios $$\frac{S'}{\Delta_m} \; \text{and} \; \frac{S'}{\Delta_m \cdot S} .$$

2. An apparatus according to claim 1 wherein the said calculating unit comprises three gates connecting the analogue digital converter respectively to three counters allotted respectively to $\Delta_m$, S and S'.

3. An apparatus according to claim 2 wherein said apparatus further includes a display unit, responsive to said calculating unit, for visually displaying the cardiac capacity.

* * * * *